United States Patent [19]

Ebata et al.

[11] Patent Number: 5,350,552
[45] Date of Patent: Sep. 27, 1994

[54] METHOD FOR PREPARING POLYACRYLAMIDE AQUEOUS GEL PLATE FOR ELECTROPHORESIS

[75] Inventors: Nobuyoshi Ebata, Takizawa; Kazuaki Notsu, Abiko; Akiko Udagawa, Tokyo; Mieko Shiratori, Abiko, all of Japan

[73] Assignee: Daiichi Pure Chemicals Co., Ltd., Tokyo, Japan

[21] Appl. No.: 9,044

[22] Filed: Jan. 26, 1993

[30] Foreign Application Priority Data

Feb. 7, 1992 [JP] Japan ................. 4-022705

[51] Int. Cl.$^5$ ............................................. B29C 39/42
[52] U.S. Cl. ................ 264/102; 204/182.8; 204/299 R; 264/297.8; 264/299; 264/331.18
[58] Field of Search ............ 204/182.8, 299 R; 264/101, 102, 299, 297.8, 331.18, 331.21

[56] References Cited

U.S. PATENT DOCUMENTS

| | | | |
|---|---|---|---|
| 3,551,541 | 12/1970 | Rossetti | 264/102 |
| 4,169,036 | 9/1979 | Anderson et al. | |
| 4,416,761 | 11/1983 | Brown et al. | 204/299 R |
| 4,810,456 | 3/1989 | Bente, III et al. | 204/182.8 |
| 4,909,977 | 3/1990 | Hurd et al. | 264/299 |
| 4,944,483 | 7/1990 | Nishizawa | 204/299 R |
| 5,069,773 | 12/1991 | Frangioni | |
| 5,188,790 | 2/1993 | Magnant | 204/182.8 |

FOREIGN PATENT DOCUMENTS

| | | | |
|---|---|---|---|
| 0334615 | 9/1989 | European Pat. Off. | |
| 9110289 | 12/1991 | Fed. Rep. of Germany | |
| 1-165949 | 6/1989 | Japan | 204/299 R |
| 4-77868 | 12/1992 | Japan | |

*Primary Examiner*—Mathieu Vargot
*Attorney, Agent, or Firm*—Bacon & Thomas

[57] ABSTRACT

A batch method for preparing polyacrylamide aqueous gels for electrophoresis, including providing a plurality of gel plate supporters abreast in an airtight gel-forming container, eliminating oxygen from or introducing oxygen-free gas into said container, charging a gel-forming solution into said container, and gelatinizing the solution. It can easily produce a large quantity of high quality polyacrylamide gel plates for electrophoresis with a homogeneous quality and a high resolving power in an automated batch method in a short period of time.

4 Claims, 3 Drawing Sheets

METHOD FOR PREPARING POLYACRYLAMIDE AQUEOUS GEL PLATE FOR ELECTROPHORESIS

BACKGROUND OF THE INVENTION

1. Field of the Invention

The present invention relates to a method for preparing a polyacrylamide aqueous gel plate for use in electrophoresis, and, more particularly, to a method for preparing a large quantity of polyacrylamide aqueous gel plates with homogeneous and high quality in a simple manufacturing procedure.

2. Description of the Background Art

Aqueous polyacrylamide gels have widely been used for electrophoresis analysis of in vivo components with a high molecular weight, e.g., protein, nucleic acid, and the like. Conventionally, polyacrylamide aqueous gels are used as electrophoresis media. They are prepared from a gel-forming solution charged into or coated onto a gel-supporter in the form of cylinder, plate, or film, or the like, on which the solution is polymerized by cross-linking to form an aqueous gel. Usually, plate-shaped gels (plate gels), which are relatively simple to prepare, easy to handle, and suitable for analyzing the plural of samples on the same conditions, are most widely used.

When preparing a gel plate, particularly in the case of a gel plate having a concentration gradient, the gel-forming solution is usually charged into each set of gel-supporter separately and individually, in most cases. According to this procedure, however, it is difficult to consistently produce a plurality of gel plates having a specified analytical performance because of the problem in the reproducibility in repeated charging. Moreover, it takes a long time and requires complicated steps to prepare a large quantity of such gel plates. In order to avoid these problems, it is necessary to introduce an expensive unit for charging of the solution and to employ a special mixing method for the preparation of gel-forming solutions. Thus, the method is not necessarily considered to be advantageous for industrial production.

On the other hand, the batch method, which utilizes a gel-forming container in which a plurality of gel-supporters are placed abreast and the gel-forming solution is charged into it to gelatinize, can afford a plurality of gel plates having the same quality by a simpler procedure as compared to the aforementioned individual, repeated charging method.

However, such batch method requires to stratify a water layer, an organic solvent layer, or the like on top of the gel-forming solution in order to prevent the gel-forming solution from contacting directly with air (oxygen) which prohibits the polymerization reaction to proceed. However, the stratified layer may mingle with the gel-forming solution producing unhomogeneous layers with different gel concentrations or a part of the layered organic solvent may remain in the gel plate. These can be the cause of deformation of electrophoresis images or deterioration of samples.

In addition, in a conventional batch method, since gel supporters are placed lengthwise in a container and the gel-forming solution is then charged full into the container, gelatinization takes place not only inside the gel supporters, but also along their peripheral portions. This often makes it difficult to take out the gel plates formed from the container or to peel off the gel plates each other. Because of this, the gel supporters may be broken or a gel supporter and the gel may be detached when they are taken out from the gel-forming container. Thus, such a conventional batch method often fails to produce an expected quantity of gel plates in a single operation. Furthermore, in the conventional batch method, the size of container or the number of supporters to be placed in a container is limited because of exothermic heat of polymerization and the like. This not only worsens the production yield and workability, but also imposes a limitation to the scale of the batch-size.

Accordingly, the present invention is to solve the above-mentioned problems in conventional batch processes and to provide a method for preparing polyacrylamide aqueous gels for electrophoresis having a high and uniform quality in a large quantity by a simple and easy procedure.

As a result of intensive studies, the present inventors found that a homogeneous gel can be obtained and deformation of electrophoresis images can be avoided by making the gel-forming container to an air-tight structure and eliminating the oxygen in the container or introducing oxygen-free gas into the container before charging the gel-forming solution. In addition, damages of gel supporters and detachment of gel and supporters at the time when they are taken out from the container can be prevented and exothermic heat of polymerization reaction can be suppressed by separating each gel supporter individually with partition members. These findings have led to the completion of the present invention.

SUMMARY OF THE INVENTION

Accordingly, an object of the present invention is to provide a batch method for preparing polyacrylamide aqueous gel plates for electrophoresis comprising: providing a plurality of gel plate supporters abreast in an airtight gel-forming container, eliminating oxygen from or introducing oxygen-free gas into said container, charging a gel-forming solution into said container, and gelatinizing the solution.

Other objects, features and advantages of the invention will hereinafter become more readily apparent from the following description.

DETAILED DESCRIPTION OF THE INVENTION AND PREFERRED EMBODIMENTS

Figure 1:
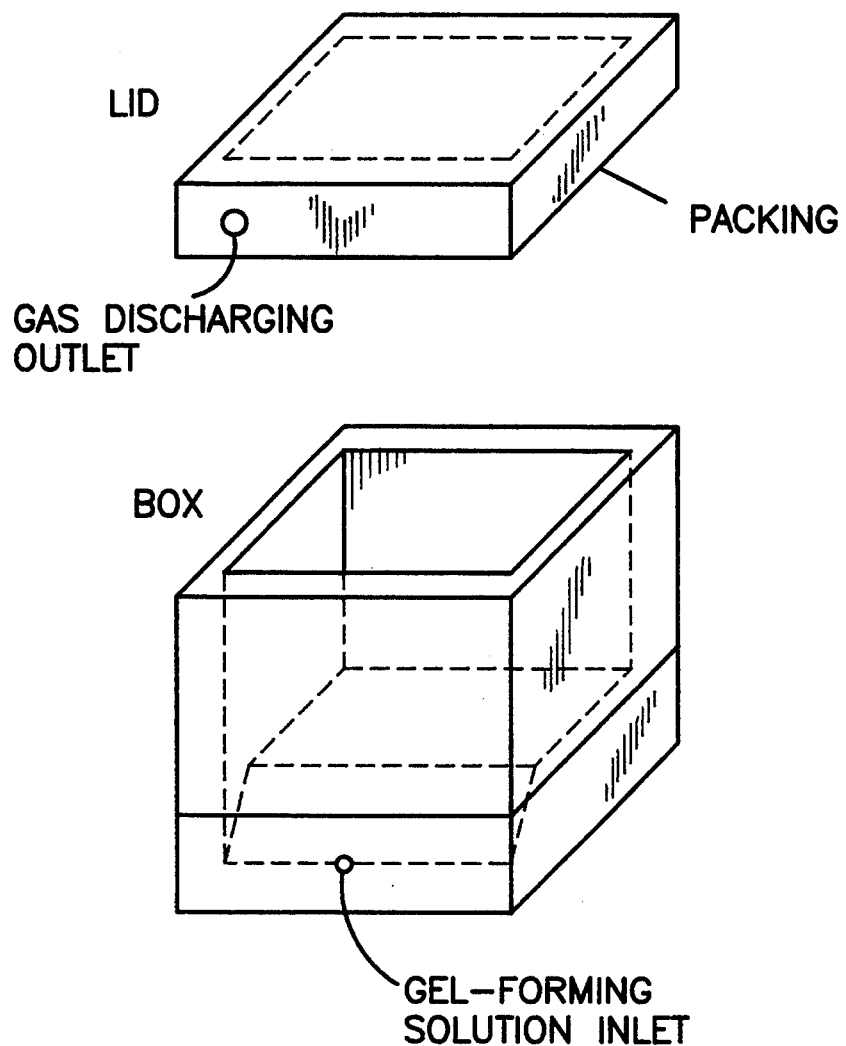
FIG. 1 shows is a view illustrating an embodiment of a lid and a box of a gel-forming container.

The gel-forming container used in the present invention is composed of a box in which gel supporters are placed and a lid which seals the container airtight, and preferably equipped with, as illustrated in FIG. 1, one or more inlet ports for a gel-forming solution and one or more outlet ports for charging gas into or discharging gas from the container. The size of the gel-forming container is determined according to the size of the gel plate supporters and the number of gel plate supporters to be used. The gel plate forming container must have an airtight structure, because it is necessary to eliminate oxygen from the container or to introduce oxygen-free gas thereinto. This airtight structure can easily be secured by applying a packing beneath the lid and providing a buckle or the like to fasten the lid and the box. The gas inlet or outlet port may be closed by a plug after the gas charging or discharging operation.

In the practice of the present invention, partition members are employed for separating gel plate supporters. The gel plate supporters do not adhere each other by the gel by the provision of partition members. In addition, generation of heat due to the polymerization reaction can be suppressed, since the partition members function as an insulator. The partition members are plates preferably made of a non-water-absorptive material, such as resin, e.g., polyethylene, polypropylene; rubber, e.g., silicone rubber, urethane rubber; or polymer resin described in the "Chemistry Handbook—Applied Chemistry Part", edited by The Chemical Society of Japan; or the like. Particularly preferred materials are porous materials which can embrace a large amount of air (oxygen) around its surface, materials with high radical adsorptivity, soft resin plates which can readily adhere to the surface of gel supporters, and the like. Specifically, a polystyrene plate, a styrene foam plate, and a fluorinated resin plate are most preferred.

Figure 2:
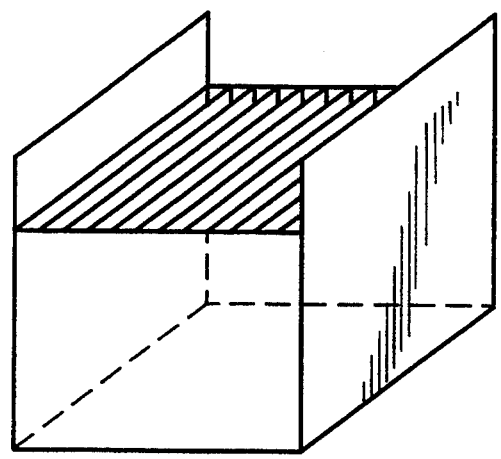
FIG. 2 is a view illustrating an embodiment of a rack for partition members.
Figure 3:
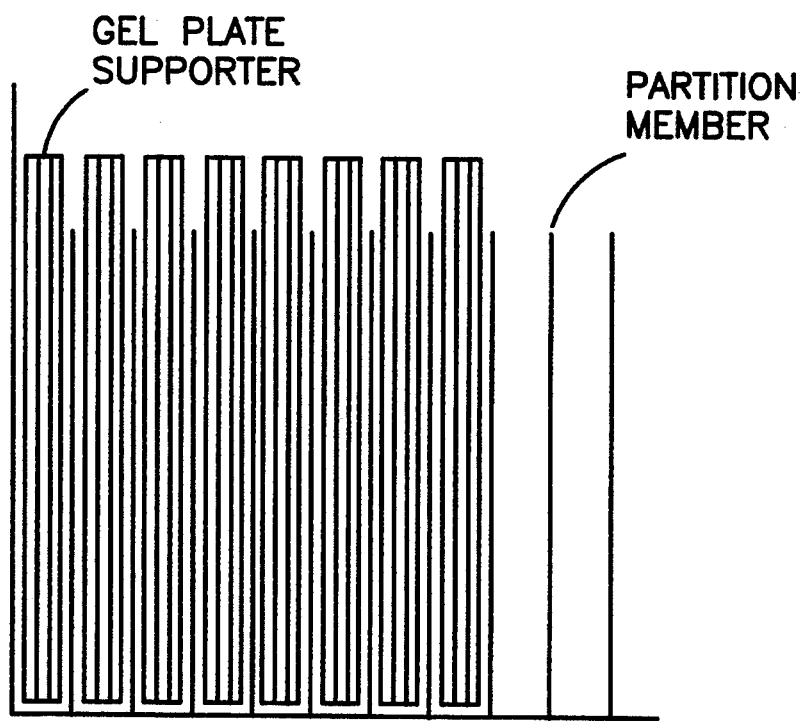
FIG. 3 is a drawing showing a partition rack wherein gel plate supporters are placed abreast.

The partition members may be placed so as to locate individual gel plate supporter separately in the gel plate forming container. It is more preferable to provide a rack for partition members, as shown in FIG. 2, in which the gel supporters are placed to stand abreast as shown in FIG. 3, and to locate the rack as a whole in the container. This construction ensures an easy and simple procedure for taking out the formed gel plates. The distance between each partition is not specifically limited provided that the gel supporters can stand individually. The partition member may have any thickness, so long as it can adequately prevent adherence of gel supporters by a sufficient amount of gel, can provide a sufficient heat insulation effect, and does not impair the analytical performance of the gel plates and the workability of the process.

Figure 4:
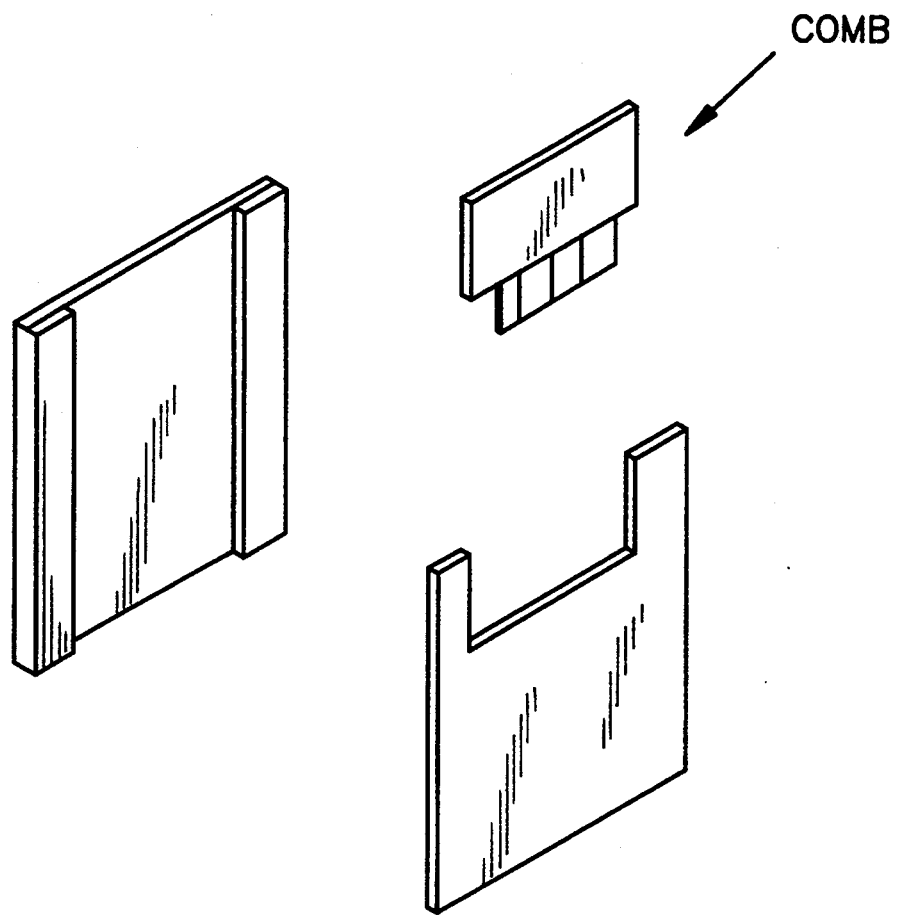
FIG. 4 is a drawing showing a broken-down gel plate supporter.

The gel plate supporter to be used in the present invention may not be particularly limited provided that an ordinary supporter is selected. For example, a mold consisting of two sheets of plates made of a non-electric conductive material (e.g., glass, plastic, etc.) arranged with a certain space between them by a frame (spacer) can be used. The mold must be provided with at least two openings for charging and discharging the gel-forming solution and the like. Specifically, as illustrated in FIG. 4, a unit consisting of two sheets of gel plates with a comb inserted between them for providing a sample slot may be used.

In the present invention, oxygen gas must be eliminated from or oxygen-free gas must be introduced into the gel-forming container after placing a plurality of gel plate supporters in the container. Oxygen gas may be removed from the container by evacuating the air confined therein by a suction device or the like. Nitrogen gas, helium gas, or the like, is preferable as an oxygen-free gas.

The target gel plate for electrophoresis can be prepared by charging a gel-forming solution into this gel-forming container and by gelatinizing. The gel-forming solution used here may be those described in known references on electrophoresis, e.g., "Electrophoresis-Fundamentals and Experiments", edited by H. Terada, or the like. Specific examples include, but not limited to, a monomer solution containing an acrylamide monomer, and as required, a cross-linking agent, an anionic surface active agent (e.g., SDS), and a pH buffering agent; a mixture of a peroxide solution and a reducing agent solution; and the like.

The electrophoresis gel plates prepared by the present invention can be applied to horizontal or vertical electrophoresis and the like according to a known method disclosed in references on electrophoresis ("Electrophoresis-Fundamentals and Experiments", edited by H. Terada; or the like). It is most suitable for use in slab-gel electrophoresis.

Other features of the invention will become apparent in the course of the following description of the exemplary embodiments which are given for illustration of the invention and are not intended to be limiting thereof.

EXAMPLES

Example 1

50 pieces of gel plate supporters (FIG. 4) were placed in a gel-forming container (FIG. 1) using a partition rack (FIG. 2), as illustrated in FIG. 3. With this arrangement, the supporters were separated from each other by polymerization prevention plates. After closing the container with a lid, nitrogen gas was injected into the container through the gel-forming solution inlet port or the gas discharging outlet port to make the inside of the container to a low-oxygen atmosphere. Conditions of the gas in the container was confirmed by measuring the amount of dissolved oxygen in the gas blown out from the container by a dissolved oxygen meter.

Then, the gel-forming solution of the following formulation was charged into the container through the gel-forming solution inlet port.

| <Formulation of the gel-forming solution> | |
| --- | --- |
| 1.5 M Tris-hydrochloride (pH 8.8) | 250 ml |
| Acrylamide | 97.5 g |
| N,N'-methylenebisacrylamide | 2.5 g |
| 1% Ammoniumperoxysulfate | 3.0 g |
| N,N,N',N'-tetramethylethylenediamine | 0.05 g |
| Water (making the total volume 1000 ml) | Balance |

After a required amount of the gel-forming solution was charged into the container, a 50% aqueous glycerol solution was filled into the container up to the bottom of the supporters and the inlet port was plugged so that the solution may not flow back. The container was allowed to stand still for a specified period of time until the content was fully gelatinized. After removing the lid, the gel plates formed were taken out altogether with the rack and subjected to an automatic washing machine. Spaces between supporters were not gelatinized with the provision of partition members, and thus each set of gel plate was easily taken out from the container. Detachment of the gels and supporters or damages to the gel plates were hardly experienced when they were taken out from the container, so that almost all of the gel plates prepared could be used for electrophoresis. Furthermore, since the surface of the gel-forming solution did not mingle with air or with a stratified liquid layer when the solution was charged into the container, high quality gel plates without flaws or stripes could be obtained.

Comparative Example 1

50 pieces of gel plates were prepared in the same manner as in Example 1, using the same gel-forming container as used in Example 1, except that the use of the partition members was omitted and a water layer on the gel-forming solution for preventing the solution from contacting air was not produced.

Gel plates prepared in Example 1 and Comparative Example 1 were examined on the following items:

(1) Time consumed for processing and taking out 50 pieces of gel plates. The washing time required for the automatic washing machine in the process of the present invention (A) was also counted and included.

(2) The number of gel plates which can be used for electrophoresis, with no supporter-gel detachment, no flaws or stripes, and no gel discoloration.

(3) Breakdown of the number of defective gels in terms of various defects.

The results are presented in Table 1.

TABLE 1

|  | Present Invention Process (A) | Conventional Method Process (B) |
|---|---|---|
| (1) Time required for processing 50 gel plates | 12 minutes | 65 minutes |
| (2) Number of gel plates usable for electrophoresis per 50 gel plates | 48 pieces | 12 pieces |
| (3) Defective gel plates (pieces) |  |  |
| a. broken supporter | 0 | 18 |
| b. detachment of supporter and gel | 0 | 10 |
| c. chipped gel plate | 1 | 5 |
| d. stripes and foams in gel plate | 1 | 4 |
| e. contamination of foreign material | 0 | 1 |

As can be seen from Table 1, the method of the present invention (A) took less than one-fifth of the processing time required for the conventional process since the method was automated as described in Example 1, whereas the conventional process (B) in Comparative Example 1 required much time and labor to take out the gel plates from the container or to peel off the gel plates from each other. Furthermore, while the conventional process produced more than ¾ unacceptable products out of 50 pieces in the outward appearance examination, the method of the present invention could produce high quality gel plates at an yield of four times or higher than that of the conventional process, only producing one defective gel plate with chipping and another defective gel plate with stripes, each found at each end of the container. This satisfactory result was due to the facts that no extreme force was needed for separating each gel plate formed, there was no mingling of the gel-forming solution with the stratified layer solution around their interface, and the like.

As illustrated above, a large quantity of high quality polyacrylamide gel plates for electrophoresis, which is homogeneous in properties and has high resolving power, can easily be prepared in a batch method in a short processing period according to the method of the present invention. In addition, procedures for taking out the gel plates after gelatinization, washing of final products, and the like, conventionally relied upon manual labor, can be automated by the suitable design of the structure of the gel-forming container, the partition members, and the like.

Obviously, further modifications and variations of the present invention are possible in light of the above teachings. It is therefore to be understood that within the scope of the appended claims, the invention may be practiced other than as specifically described herein.

What is claimed is:

1. A batch method for preparing a polyacrylamide aqueous gel plate for electrophoresis comprising:
   (1) placing a plurality of gel plate supporters in a gel-forming container which comprises:
      (a) a partition rack comprised of plastic or rubber partition members which separate the gel plate supporters from each other,
      (b) an inlet port,
      (c) an outlet port, and
      (d) an airtight lid;
   (2) closing the airtight lid;
   (3) eliminating oxygen from the container by evacuating air through the outlet port;
   (4) charging a gel-forming solution into the container through the inlet port;
   (5) allowing the gel-forming solution to gelatinize on the gel plate supporters;
   (6) removing the partition rack from the container; and
   (7) removing the individual gel plates from the partition rack.

2. A batch method according to claim 1 wherein the partition members are comprised of polystyrene, styrene foam or fluorinated resin.

3. A batch method according to claim 2 wherein the partition members are in the form of plates.

4. A batch method according to claim 1 wherein the partition members are of sufficient height and thickness to prevent adherence of adjacent gel plate supporters and to provide a sufficient insulation effect to suppress generation of heat of polymerization.

* * * * *